United States Patent [19]

Harvey

[11] 4,080,191

[45] Mar. 21, 1978

[54] AQUATIC PESTICIDAL COMPOSITIONS AND METHOD

[75] Inventor: John Charles Harvey, Kendall Lakes, Fla.

[73] Assignee: Sandoz Ltd., Basel, Switzerland

[21] Appl. No.: 374,880

[22] Filed: Jun. 29, 1973

[30] Foreign Application Priority Data

Jun. 30, 1972 Switzerland .......................... 9844/72
Jul. 4, 1972 Switzerland .......................... 9987/72
Nov. 6, 1972 United Kingdom ................ 51005/72

[51] Int. Cl.² .................. A01N 9/22; A01N 9/36
[52] U.S. Cl. ......................................... 71/92; 71/93; 71/109; 71/116; 71/118; 71/120; 71/121; 71/124; 71/125; 424/200; 424/285; 424/300
[58] Field of Search .................... 424/200, 300; 71/92, 71/109

[56] References Cited

U.S. PATENT DOCUMENTS 3,810,980 5/1974 Pohlmann et al. ................... 424/200

OTHER PUBLICATIONS

McCutcheon's Detergents & Emulsifiers, p. 96 (1968).
Gunther et al.—Modern Insecticides & World Food Production, pp. 65–67 (1960).

*Primary Examiner*—Leonard Schenkman
*Attorney, Agent, or Firm*—Gerald D. Sharkin; Richard E. Vila

[57] ABSTRACT

The present invention concerns a pesticidal formulation which comprises, in admixture, a pesticidal agent, an anionic or non-ionic surfactant and a water-immiscible solvent/diluent, the formulation being adapted to form a slick on a water surface. The formulation is useful in combating pests on or directly beneath water.

54 Claims, No Drawings

AQUATIC PESTICIDAL COMPOSITIONS AND METHOD

The present invention relates to pesticidal formulations and more specifically to pesticidal formulations adapted to combat pests in a water locus. In particular, the present invention relates to pesticidal formulations suitable for combating insects or undesired plant growth in a water locus.

It is now known that a number of insects, which, at some stage in their development, inhabit stagnant or running water, pools and sewage, are responsible for the transmission of many infections and parasitic diseases. In addition, it is known that crops cultured in a water locus, e.g. rice, are subject to attack by insects, which at some stage in their development inhabit the water locus. It is also known that many of such insects, at some stage in their development e.g. the larval stage, live on or directly beneath the water surface.

In addition, the presence of aquatic weeds in waters such as rivers, canals, lakes and drainage channels present serious problems in view of obstructed water flow or passageways. It is known that such problems are largely caused by floating and emergent species of aquatic weed, i.e. aquatic weeds having leaves that float on the surface of the water or aquatic weeds having aerial stems and leaves protruding above the water surface.

As will be readily appreciated, the combating of such pests, i.e. pests residing on or directly beneath the water surface poses serious difficulties. For example, the activity of a pesticide is much reduced with reduction of the concentration thereof. Thus, the dissolution or suspension of a conventional pesticidal formulation in the water locus will be ineffective to combat pests, unless the amounts employed are exceedingly high. Quite apart from economic considerations, at such amounts, serious polution problems may arise, e.g. unacceptably high levels of phytotoxicity or animal toxicity in the water may occur. Moreover, such problems are aggravated by uneven distribution of the pesticide in the water, when conventional pesticidal formulations are employed.

The present invention is directed to the problem of providing a pesticidal formulation suitable for use in combating pests residing on or directly beneath a water surface.

Accordingly, the present invention provides a pesticidal "slick" formulation which comprises 5 to 60% by weight of a pesticidal agent, 0.2 to 4% by weight of an anionic or non-ionic surfactant having an HLB value of less than 12.5, and the balance to 100% by weight being a water-immiscible solvent/diluent having a mean specific gravity of less than 1.

The abbrevation "HLB" as used herein is a term of art meaning hydrophilic/lipophilic balance, being an index representing the relative hydrophilic/lipophilic character of the surfactant.

It is to be understood that by the term "slick" as used herein is meant a film, evenly formed on the surface of a water locus, and by the term "pesticidal slick formulation" as used herein is meant a pesticidal formulation adapted to distribute itself evenly over the surface of a water locus as a film. Thus, the formulation itself will also have a mean specific gravity of less than 1.

Preferably, the "slick" formulation comprises 5 to 55%, especially 5 to 50%, and more preferably 10 to 50%, by weight of the pesticidal agent.

Preferably, the "slick" formulation comprises 0.2 to 3.5%, more preferably 2 to 3.5%, by weight of the surfactant.

A quantative measure of the "slick" forming ability of the formulations of the invention is the "spreading co-efficient" S(dyn/cm) thereof, which is defined as follows, viz:

$$S = (\gamma_{f/A} + \gamma_{f/w}) - \gamma_{w/A}$$

wherein $\gamma_{f/A}$ signifies the interfacial surface tension between the formulation and air, $\gamma_{f/w}$ signifies the interfacial surface tension between the formulation and water, and $\gamma_{w/A}$ signifies the interfacial surface tension between water and air.

The spreading co-efficient may be determined in accordance with known methods and using conventional apparatus.

It has been found that the "slick" formulations of the present invention have positive spreading co-efficients.

In addition, while the optimum proportions of the pesticidal agent, the surfactant and the solvent/diluent, will depend on the actual constituents employed, generally, increasing positive values of the spreading co-efficient of the formulation improves the "slick" forming ability thereof and thus the proportions of the constituents employed are advantageously determined with reference to the spreading co-efficient of the formulation, that is to say, the proportions of the constituents are advantageously arranged to achieve a relatively high positive spreading co-efficient value. Formulations having a spreading co-efficient of over 5 e.g. over 10, and more particularly over 15, preferably between 20 and 30, dyn/cm, are found in practice to have particularly useful "slick" forming characteristics and "slick" stability.

The type of pesticide employed in the formulations can vary within wide limits. Thus, with regard to insecticides, organophosphate insecticides e.g. phosphoric acid esters such as O,O-dimethyl-O-[quinoxalyl-(2)]-thionophosphate and O,O-diethyl-O-[quinoxalyl-(2)]-thionophosphate, or carbamate type insecticides, e.g. 2-isopropoxyphenyl-N-methylcarbamate and 2,3-dihydro-2,2-dimethyl-7-benzofuranyl methyl carbamate, may be mentioned as examples. With regard to herbicides, there may be mentioned as examples triazines e.g. 2-chloro-4-ethyl-amino-6-isopropylamino-S-triazine, phenylureas e.g. 3-[p-(p-chlorophenoxy)phenyl]-1,1-dimethylurea or 3-[m-chloro-p-methoxyphenyl]-1,1-dimethylurea, benzamides, anilides e.g. 3,4-dichloropropionanilide, 2,4-dinitrophenyls, diphenyl ethers, e.g. 2,4'-dinitro-4-trifluoromethyl diphenyl ether, pyridazones, e.g. 5-amino-4-chloro-2-phenyl-3(2H)-pyridazinone or (4-chloro-5-dimethylamino)-2-$\alpha,\alpha,\alpha$-trifluoro-m-tolyl-3(2H)-pyridazinone, uracils, e.g. 5-bromo-3-sec.butyl-6-methyluracil, and phenoxy aliphatic acids and derivatives, e.g. 2-methyl-4-chlorophenoxy acetic acid and the iso-octyl ester thereof, as well as plant growth retarding agents such as phenoxy aliphatic acids.

In general, the type of pesticide is selected primarily in relation to the pest to be controlled. In relation to the "slick" formulations of the invention, in general, the nature of the pesticide will not significantly disturb the "slick" forming ability of the formulation. Naturally, however, in the case of water soluble pesticides, some precaution should be taken to prevent rapid transfer of pesticide from the "slick" layer to the water, if this is undesirable. For this reason, water insoluble or sparingly soluble pesticides are preferred. However, water soluble pesticides may be employed, either when rapid transfer into the water is desirable, e.g. to achieve uniform distribution of the pesticidal agent, or, if appropriately formulated to prevent rapid transfer, e.g. by micro-encapsulation of the formulation or by employing some other carrier pack form of formulation (i.e. sustained release form). Indeed, sustained release (e.g. micro-encapsulated) forms of formulations may advantageously be employed in general, e.g. to continuously compensate for pesticidal loss in the "slick" layer, avoiding the necessity of high quantities of free pesticide in the "slick" layer, enabling a "slick" layer of longer effective life.

As regards the surfactant constituent of the "slick" formulation of the invention, any of the available anionic or non-ionic surfactants having an HLB value of less than 12.5 may be employed. Examples of suitable surfactants are set out below:

| Surfactant (Trade name) | Chemical composition | HLB value |
|---|---|---|
| Tetronic 702 | Propylene-oxide/ethylene diamine/ethylene-oxide copolymer | 7.0 |
| Span 20 | Sorbitol monolaurate | 8.6 |
| Triton X-363 | Alkylarylpolyether-ethanol | 9.1 |
| Tween 61 | Polyoxyethylene sorbitol monostearate | 9.6 |
| Atlox 3404 F | Polyoxyethylene sorbitol oleate laurate | 10.0 |
| Atlas G 1086 | Polyoxyethylene sorbitol hexaoleate | 10.2 |
| Tergitol NP-16 | Nonylphenylpolyethylene glycol ether | 10.9 |
| Pluronic L 63 | Condensate of ethylene oxide with hydrophobic precondensate formed by condensing propylene oxide with propylene glycol | 11.0 |
| Atlas G-1096 | Polyoxyethylene sorbitol hexaoleate | 11.4 |
| Pluronic L 43 | Condensate of ethylene oxide with hydrophobic precondensate formed by condensing propylene oxide with propylene glycol | 12.0 |

Preferred surfactants are the commercially available polyoxyethylene ether surfactants, polyoxyethylene fatty acid ester surfactants, or the blend polyoxyethylene ether or fatty acid ester/alkylarylsulphonate surfactants, having HLB values of less than 12.5, particularly the blend polyoxyethylene ether/aralkyl sulphonate surfactant (HLB value less than 12.5) commercially available under the trade name Emcol N 141 B (Witco Chemical Corporation, New York, U.S.A.).

With regard to the solvent/diluent constituent of the "slick" formulation of the invention, from the point of view of economy, preferably, an essentially two component liquid system is employed, the one component acting, primarily, as a solvent, and the other component acting, primarily, as a diluent.

Preferred solvent components of such two component systems are aromatic petroleum fractions, e.g. Shellsol A (Trade name), an aromatic hydrocarbon petroleum fraction having a boiling range of 161°–182° C, Shellsol AB (Trade name), an aromatic hydrocarbon petroleum fraction having a boiling range of 187°–213° C, Shellsol R (Trade name), an aromatic hydrocarbon petroleum fraction having a boiling range of 203°–267° C, Solvesso (Trade name), an aromatic hydrocarbon petroluem fraction having a boiling range of 187°–212° C, Panasol (Trade name), an aromatic hydrocarbon petroleum fraction having a boiling range of 130°–220° C (90–100% aromatics), and high boiling or high molecular weight aromatic naphthas (known in the art as HAN). Further preferred solvent components are aromatic hydrocarbon petroleum fractions, e.g. xylene, toluene and methyl-naphthalene. Liquid and water immiscible phenols such as nonyl phenol (technical grade), a mixture of monoalkyl phenols, predominantly para-substituted, the side chains being branched alkyl radicals, having a boiling range of 292°–297° C, are further examples of suitable solvents. Furthermore, the solvent component may itself comprise a mixture of solvents, e.g. a mixture of xylene and nonyl phenol (technical grade).

Preferred diluent components of the abovementioned two component solvent/diluent system are hydrocarbon petroleum fractions, particularly aliphatic hydrocarbon petroleum fractions, e.g. kerosene having a boiling range of between 175° and 288° C, or Varsol (Trade name — common names "test benzene" or "white spirit"), mainly an aliphatic saturated hydrocarbon petroleum fraction containing between 17 and 18% aromatics, having a boiling range of 140°–200° C.

In such two component solvent/diluent systems, the ratio by weight of solvent:diluent is preferably from 2:1 to 1:3.5, more preferably from 1.5:1 to 1:1.

However, it is to be understood that a two component solvent/diluent system is not essential, the prime consideration being an economic one, and indeed an essentially one component solvent system may be of advantage, the solvent being employed in such quantity as to simultaneously serve as diluent for the formulation. Examples of suitable solvents correspond to those listed above in relation to the essentially two component solvent/diluent system. Moreover, the essentially one component solvent system may itself comprise a mixture of solvents, e.g. xylene/nonyl phenol (technical grade).

The pestidical "slick" formulations of the present invention may be used by application to a water locus afflicted with the pest to be combated in much the same way as conventional liquid forms of pesticides are applied. Thus, the formulations may be misted, sprayed or poured onto the water locus using conventional application equipment. However, the pesticidal "slick" formulations of the invention are particularly well suited to low-volume application techniques. In the case when the formulation is employed in carrier pack form, e.g. micro-encapsulated form, conventional methods of applying such forms are appropriate.

It is found in practice that the "slick" formulation of the invention is self-distributing, that is to say, on application of the formulation to the water locus, the "slick" automatically distributes itself over a considerable area of the water surface in the form of an evenly distributed and coherent film, such that, within practical limits, the pesticidal component of the formulation is not localised in patches over the water surface, but is advantageously effective over a complete area. Indeed, this advantage reduces the necessity of even application of the formulation over the water surface.

The amount of the formulation employed will naturally depend on the proportion of pesticidal agent in the formulation, the nature of the pest and pesticide and the type of water locus. However, in general, satisfactory results are obtained when the amount of active agent per unit area of water locus is in the range of 1 to 10 kg/hectare.

Examples of formulations of the invention are as follows:

EX. 1. INSECTICIDAL "SLICK" FORMULATION EXAMPLE 42.8 Parts by weight of an insecticide are mixed with 2 parts by weight of a surfactant consisting of polyoxyethylene ether blended with an oil soluble alkylaryl sulphonate and sold under the trade name Emcol N 141 B, 21.2 parts by weight of xylene and 34 parts by weight of kerosene with a boiling range of 175°–288° C, whereby a clear concentrate is obtained. The formulation has a positive spreading co-efficient value.

The formulation produced in accordance with the above example was misted over the surface of an area of still water using a mist generator. A coherent evenly distributed "slick" rapidly spread over the surface of the water which was not emulsified by the water.

100 ml. of the formulation produced in accordance with the above formulation example was sprayed on an irrigated rice allotment having a size of 10 × 50 m². The application was effected by means of a "Solo"-sprayer adapted for LV application. The rice plants were strongly infected with the rice stem borer (*Chilo suppressalis*) in the larval and adult stages. An evenly distributed film spread on the surface, especially around the various rice plants.

After each of 4 applications and again before harvest, the rice plants were checked with regard to the infestation produced by the rice stem borer. The percentage infestation was determined by "dead hearts" and "white ears" evaluation. The treatment of the plants significantly reduced the number of the infected plants. An untreated control allotment similar in situation, size and original infestation was employed for comparison purposes.

EX. 2. HERBICIDAL "SLICK" FORMULATION EXAMPLE

13 Parts by weight of (4-chloro-5-dimethylamino)-2-α,α,α-trifluoro-m-tolyl-3(2H)-pyridazinone are mixed with 3,2 parts by weight of a surfactant comprising polyoxyethylene ether blended with an oil soluble alkylaryl sulphonate and sold under the trade name Emcol N 141 B, 62,3 parts by weight of xylene and 21,5 parts by weight of nonyl phenol (technical grade). The formulation has a positive spreading co-efficient value.

The herbicidal formulation of the preceding example was sprayed from an aeroplane by means of a commercial spraying device adapted for LV-application on a lake whose surface was covered with Eichhornia crassipes. 3 kg of active agent per hectare of water surface was thus applied.

A coherent evenly distributed "slick" rapidly spread over the surface of the waater which was not emulsified by the water. After 2 – 3 weeks, new shoots were marked by a lack of chlorophyll. After 4 – 5 weeks a significant herbicidal effect was observed.

EX. 3. HERBICIDAL "SLICK" FORMULATION EXAMPLE 52.2 Parts of 2-methyl-4-chloro-phenoxy iso-octyl acetate, 21.7 parts by weight of a diluent commercially available under the trade name Varsol [common names "test benzene" or "white spirit" and comprising mainly an aliphatic saturated hydrocarbon petroleum fraction and containing between 17 – 18% of aromatics, the diluent having a boiling range of 140° to 200° C], 22.8 parts by weight of xylene and 3.3 parts by weight of Emcol N 141 B (Trade name — see Examples 1 and 2above) as surfactant were mixed together to obtain a homogeneous solution.

The formulation so obtained has a positive spreading co-efficient.

The formulation so obtained was misted on a water surface using a mist generator. An evenly distributed "slick" formed on the water surface which was stable and not emulsified by the water.

EX. 4. HERBICIDAL "SLICK" FORMULATION EXAMPLE 52.2 Parts by weight of 2-methyl-4-chloro-phenoxy iso-octyl acetate, 10.8 parts by weight of a diluent commercially available under the Trade name Varsol [see Example 3], 33.6 parts by weight of xylene, and 3.4 parts by weight of Emcol N 141 B [Trade name — see Examples 1 and 2] were mixed together until a homogeneous solution was obtained.

The formulation so obtained has a positive spreading co-efficient.

The formulation so obtained was misted on a water surface using a mist generator. An evenly distributed "slick" formed on the water surface which was stable and not emulsified by the water.

EX. 5. HERBICIDAL "SLICK" FORMULATION EXAMPLE a. The Varsol (Trade name) diluent of Examples 3 and 4 was replaced by the same weight of
  (i) kerosene, or
  (ii) Shellsol R [Trade name — an aromatic hydrocarbon petroleum fraction having a boiling range 203°–267° C, having approximate composition, 67% alkylbenzene ($C_{10}$–$C_{14}$), 6% monocycloalkyl benzene (e.g. 5-methyl-hydrindene) and 9% aromatics of ill-defined description ($C_{14}$ and above)].

The resulting formulations have positive spreading co-efficients.

In each case, the resulting formulations behaved, on application to water, in similar manner to the formulations of Examples 3 and 4.

EX. 6. HERBICIDAL "SLICK" FORMULATION EXAMPLE

In the formulations of Examples 3, 4 and 5, the xylene solvent was replaced with the same weight of Panasol [Trade name — an aromatic hydrocarbon petroleum fraction (90 – 100% aromatics), having a boiling range 130°–220° C].

The resulting formulations have positive spreading co-efficients.

In each case, the resulting formulations behaved, on application to water, in similar manner to the formulations of Examples 3, 4 and 5.

What is claimed is:

1. A pesticidal "slick" formulation comprising: (a) 5 to 60% by weight of a pesticidal agent, (b) 0.2 to 4% by weight of a surfactant selected from the group consisting of an anionic surfactant, a non-ionic surfactant and mixtures thereof, said surfactant having an HLB value of less than 12.5, and (c) a water-immiscible solvent/diluent selected from the group consisting of a water-immiscible solvent, a water-immiscible solvent with one or more water-immiscible diluents and mixtures thereof, said water-immiscible solvent/diluent having a mean specific gravity of less than 1 and being present in an amount to make up the balance to 100% by weight; the proportions of said constituents (a), (b) and (c) being such that said formulation has a positive spreading co-efficient value.

2. The formulation of claim 1, wherein the pesticidal agent is an insecticidal agent.

3. The formulation of claim 2, wherein the insecticidal agent is an organophosphate.

4. The formulation of claim 3, wherein the organophosphate is selected from the group consisting of O,O-dimethyl-O-[quinoxalkyl-(2)]-thionophosphate and O,O-diethyl-O-[quinoxalyl-(2)]-thionophsophate.

5. The formulation of claim 1, wherein the pesticidal agent is a herbicidal agent.

6. The formulation of claim 5, wherein the herbicidal agent is selected from the group consisting of a pyradazinone and a phenoxy aliphatic acid derivative.

7. The formulation of claim 6, wherein the pyradazinone is (4-chloro-5-dimethylamino)-2,$\alpha,\alpha,\alpha$-trifluoro-m-tolyl-3(2H)-pyridazinone and the phenoxy aliphatic acid derivative is 2-methyl-4-chloro-phenoxy iso-octyl acetate.

8. The formulation of claim 1, wherein the surfactant is selected from the group consisting of:
  a. a propylene oxide/ethylene-diamine/ethylene-oxide copolymer having an HLB value of 7.0,
  b. a sorbitol monolaurate having an HLB value of 8.6,
  c. an alkylaryl polyether-ethanol hving an HLB value of 9.1,
  d. a polyoxyethylene sorbitol monostearate having an HLB value of 9.6,
  e. a polyoxyethylene sorbitol oleate laurate having an HLB value of 10.0,
  f. a polyoxyethylene sorbitol hexaoleate having an HLB value 10.2,
  g. a nonylphenylpolyethylene glycol ether having an HLB value of 10.9,
  h. a condensate of ethylene oxide with a hydrophobic precondensate formed by condensing propylene oxide with propylene glycol, having an HLB value of either 11.0 or 12.0,
  i. a polyethylene sorbitol hexaoleate having an HLB value of 11.4,
  j. a polyethylene ether having an HLB value of less than 12.5,
  k. a polyoxyethylene fatty acid ester having an HLB value of less than 12.5, and
  l. a blend polyoxyethylene ether or fatty acid ester/alkylaryl sulphonate having an HLB value of less than 12.5.

9. The formulation of claim 8, wherein the surfactant is selected from the group consisting of a polyoxyethylene ether having an HLB value of less then 12.5, a polyoxyethylene fatty acid ester having an HLB value of less than 12.5, and a blend polyoxyethylene ether or polyoxyethylene fatty acid ester/alkylaryl sulphonate having a mean HLB value of less than 12.5.

10. The formulation of claim 9, wherein the surfactant is a blend of polyoxyethylene ether/alkylaryl sulphonate having a mean HLB value of less than 12.5.

11. The formulation of claim 1, wherein the solvent/diluent consists of a mixture of a solvent and a diluent.

12. The formulation of claim 11, wherein the solvent comprises an aromatic hydrocarbon petroleum fraction.

13. The formulation of claim 12, wherein the aromatic hydrocarbon petroleum fraction has a boiling range of 130°–220° C, 161°–182° C, 187°–213° C or 203°–267° C.

14. The formulation of claim 12, wherein the aromatic hydrocarbon petroleum fraction is a high boiling aromatic naphtha.

15. The formulation of claim 12, wherein the aromatic hydrocarbon petroleum fraction is xylene, toluene or methyl-naphthalene.

16. The formulation of claim 11, wherein the solvent is a liquid, water-immiscible phenol.

17. The formulation of claim 16, wherein the phenol is technical grade nonyl phenol.

18. The formulation of claim 11, wherein the solvent itself comprises a mixture of separate constituents.

19. The formulation of claim 18, wherein the solvent consists of a mixture of xylene and nonyl phenol (technical grade).

20. The formulation of claim 11, wherein the diluent comprises an aliphatic hydrocarbon petroleum fraction.

21. The formulation of claim 20, wherein the aliphatic hydrocarbon petroleum fraction has a boiling range of 175° to 288° C or 140° to 200° C.

22. The formulation of claim 21, wherein the aliphatic hydrocarbon petroleum fraction is kerosene having a boiling range of 175° to 288° C.

23. The formulation of claim 1, wherein the solvent/diluent consists of a solvent which also serves as a diluent.

24. The formulation of claim 23, wherein the solvent is a mixture of solvents.

25. The formulation of claim 1, wherein the proportion of each constituent is arranged to provide a spreading co-efficient of at least +5 dyn/cm.

26. The formulation of claim 25, wherein the spreading co-efficient is in the range of from +5 to +30 dyn/cm.

27. The formulation of claim 26, wherein the spreading co-efficient is in the range of from +10 to +30 dyn/cm.

28. The formulation of claim 27, wherein the spreading co-efficient is in the range of from +20 to +30 dyn/cm.

29. The method of combating pests on or in a water locus comprising applying to the surface of the water locus a pesticidal formulation comprising: (a) 5 to 60% by weight of a pesticidal agent, (b) 0.2 to 4% by weight of a surfactant selected from the group consisting of an anionic surfactant, a non-ionic surfactant and mixtures thereof, said surfactant having an HLB value of less than 12.5, and (c) a water-immiscible solvent/diluent selected from the group consisting of a water-immiscible solvent, a water-immiscible solvent with one or more water-immiscible diluents and mixtures thereof, said water-immiscible solvent/diluent having a mean specific gravity of less than 1 and being present in an amount to make up the balance to 100% by weight; the proportions of said constituents (a), (b) and (c) being such that said formulation has a positive spreading co-efficient value, whereby said formulation distributes itself over water surface areas not covered by such initial application.

30. The method of claim 29 wherein the spreading co-efficient is in the range of plus 10 to plus 30 dyn/cm.

31. The method of claim 29 wherein the surfactant is selected from the group consisting of:
   a. a propylene oxide/ethylene-diamine ethylene-oxide copolymer having an HLB value of 7.0,
   b. a sorbitol monolaurate having an HLB value of 8.6,
   c. an alkylaryl polyether-ethanol having an HLB value of 9.1,
   d. a polyoxyethylene sorbitol monostearate having an HLB value of 9.6,
   e. a polyoxyethylene sorbitol oleate laurate having an HLB value of 10.0,
   f. a polyoxyethylene sorbitol hexaoleate having an HLB value of 10.2,
   g. a nonylphenylpolyethylene glycol ether having an HLB value of 10.9,
   h. a condensate of ethylene oxide with a hydrophobic precondensate formed by condensing propylene oxide with propylene glycol, having an HLB value of either 11.0 or 12.0,
   i. a polyethylene sorbitol hexaoleate having an HLB value of 11.4,
   j. a polyethylene ether having an HLB value of less than 12.5,
   k. a polyoxyethylene fatty acid ester having an HLB value of less than 12.5, and
   l. a blend polyoxyethylene ether or fatty acid ester-/alkylaryl sulphonate having an HLB value of less than 12.5.

32. The method of claim 31 wherein the surfactant is selected from the group consisting of a polyoxyethylene ether having an HLB value of less than 12.5, a polyoxyethylene fatty acid ester having an HLB value of less than 12.5, and a blend polyoxyethylene ether or polyoxyethylene fatty acid ester/alkylaryl sulphonate having a mean HLB value of less than 12.5.

33. The method of claim 32 wherein the surfactant is a blend polyoxyethylene ether/alkylaryl sulphonate having a mean HLB value of less than 12.5.

34. The method of claim 29 wherein the solvent/diluent consists of a mixture of a solvent and a diluent.

35. The method of claim 34 wherein the solvent comprises an aromatic hydrocarbon petroleum fraction.

36. The method of claim 35 wherein the aromatic hydrocarbon petroleum fraction has a boiling range of 130°–220° C, 151°–182° C, 187°–213° C or 203°–267° C.

37. The method of claim 35 wherein the aromatic hydrocarbon petroleum fraction is a high boiling aromatic naphtha.

38. The method of claim 35 wherein the aromatic hydrocarbon petroleum fraction is xylene, toluene or methyl-naphthalene.

39. The method of claim 34 wherein the solvent is a liquid, water-immiscible phenol.

40. The method of claim 39 wherein the phenol is technical grade nonyl phenol.

41. The method of claim 34 wherein the solvent itself comprises a mixture of separate constituents.

42. The method of claim 41 wherein the solvent consists of a mixture of xylene and nonyl phenol (technical grade).

43. The method of claim 34 wherein the diluent comprises an aliphatic hydrocarbon petroleum fraction.

44. The method of claim 43 wherein the aliphatic hydrocarbon petroleum fraction has a boiling range of 175° to 288° C or 140° to 200° C.

45. The method of claim 44 wherein the aliphatic hydrocarbon petroleum fraction is kerosene having a boiling range of 175° to 288° C.

46. The method of claim 29 wherein the solvent/diluent consists of a solvent which also serves as a diluent.

47. The method of claim 46 wherein the solvent is a mixture of solvents.

48. The method of claim 29 wherein the proportion of each constituent is arranged to provide a spreading co-efficient of at least +5 dyn/cm.

49. The method of claim 48 wherein the spreading co-efficient is in the range of from +5 to +30 dyn/cm.

50. The method of claim 30 wherein the spreading co-efficient is in the range of from +20 to +30 dyn/cm.

51. The method of claim 29 wherein the pesticidal agent is an insecticidal agent.

52. The method of claim 51 wherein the pesticidal agent is selected from the group consisting of O,O-dimethyl-O-[quinoxalyl-(2)]-thionophosphate and O,O-diethyl-O-[quinoxalyl-(2)]-thionophosphate.

53. The method of claim 29 wherein the pesticidal agent is a herbicidal agent selected from the group consisting of a pyradazinone and a phenoxy aliphatic acid derivative.

54. The method of claim 53 wherein the pyradazinone is (4-chloro-5-dimethylamino-2,$\alpha,\alpha,\alpha$-trifluoro-m-tolyl-3(2H)-pyridazinone and the phenoxy aliphatic acid derivative is 2-methyl-4-chlorophenoxy iso-octyl acetate.

* * * * *